United States Patent [19]

Brandes et al.

[11] Patent Number: 4,829,068

[45] Date of Patent: May 9, 1989

[54] TREATMENT OF DISORDERS OF THE GASTRO-INTESTINAL TRACT

[75] Inventors: Lorne J. Brandes, Winnipeg; Gary B. Glavin, Headlingly, both of Canada

[73] Assignee: University of Manitoba, Winnipeg, Canada

[21] Appl. No.: 27,241

[22] Filed: Mar. 18, 1987

[51] Int. Cl.$^4$ .................. A61K 31/135; A61K 31/54
[52] U.S. Cl. ................................. 514/239.2; 514/648
[58] Field of Search ............................. 514/648, 239.2

[56] References Cited

PUBLICATIONS

Application No. 85.300994.2.

*Primary Examiner*—Frederick E. Waddell
*Attorney, Agent, or Firm*—Sim & McBurney

[57] ABSTRACT

Diphenylmethanes of the formula I:

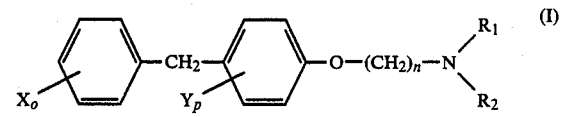

wherein X and Y are each chlorine or bromine, o and p are 0 or 1, $R_1$ and $R_2$ are each alkyl groups containing from 1 to 3 carbon atoms or are joined together to form a hetero-ring with the nitrogen atom and n is 1, 2 or 3, are effective in the alleviation and prevention of stress- and irritant-induced ulcers in the gastro-intestinal tract. A particularly useful compound is DPPE.

10 Claims, No Drawings

TREATMENT OF DISORDERS OF THE GASTRO-INTESTINAL TRACT

FIELD OF INVENTION

The present invention provides a novel treatment for ulcer disorders of the gastro-intestinal tract using certain chemicals.

BACKGROUND TO THE INVENTION

Gastro-intestinal ulceration is very common and affects many individuals. Gastro-intestinal ulceration may be brought about by acute stress or by acute or chronic ingestion of irritants, for example, alcohol, or by excess stomach acid secretion (hyperacidity). Excess acid production usually stems from a combination of factors, including stress, poor diet and improper eating habits.

Milder forms of excess acid production, manifested by upset stomach, heartburn and the like, can be treated by a wide range of proprietary anti-acid preparations, and lead to temporary relief.

Ulcerous conditions due to any cause are more difficult to treat and generally involve adherence to a strict dietary regimen, along with the administration of medication. The medicament most commonly prescribed is cimetidine, sold under the trade mark "Tagamet". "Tagamet" is particularly useful in treating cases due to hyperacidity.

More recently, synthetic prostaglandin compounds have been introduced for the treatment of ulcers, for example, that sold under the trade mark "Cytotec" by Searle Pharmaceuticals.

SUMMARY OF INVENTION

We have surprisingly found that certain tertiary amino alkylene-oxy- derivatives of diphenyl methane are effective in attenuating acute gastric ulcer formation caused both by stress and by irritants and in significantly decreasing gastric acid production, and at dosage levels significantly below those of the prototype therapeutic agent, cimetidine.

The compounds which are used in the present invention correspond to the formula (I):

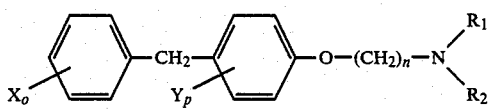

wherein X and Y are each chlorine or bromine, o and p are 0 or 1, $R_1$ and $R_2$ are each alkyl groups containing from 1 to 3 carbon atoms or are joined together to form a hetero-ring with the nitrogen atom and n is 1, 2 or 3.

One specific compound with which extensive testing has been conducted is N,N-diethyl-2-[(4-phenylmethyl)phenoxy]ethanamine HCl (DPPE for short), i.e. the compound wherein o and p are each 0, n is 2, and $R_1$ and $R_2$ are each ethyl groups.

Since the compounds act both to decrease gastric acid production in the gastrointestinal tract and to protect the integrity of the gastric mucosa, compositions containing the same may be employed to prevent ulcer formation caused by hyperacidity or by irritants, such as alcohol, in a healthy patient and also to promote the natural healing of ulcers in a patient.

U.S. Pat. No. 2,703,324 describes certain compounds similar to DPPE and specifically discloses the dimethyl homolog. The compounds are described in this prior art as anesthetics, antihistamines and antifungals. Chemical Abstracts 50, 7092g describes both DPPE and its dimethyl homolog as having antihistamine properties. In published European Patent Application No. 85.300994.2, there is described the use of DPPE as an antiproliferative agent in the treatment of cancer, notably breast cancer.

There is nothing in these prior art disclosures which would suggest that DPPE or its analogs, as described below, would in any way be effective in the treatment and prevention of gastro-intestinal disorders.

GENERAL DESCRIPTION OF INVENTION

As mentioned above, the compounds which are employed in the present invention are diphenylmethane derivatives having tghe general formula I:

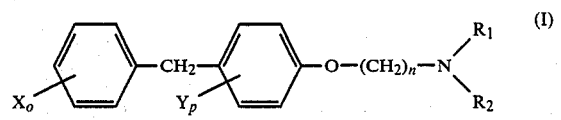

wherein X and Y are each chlorine or bromine, o and p are 0 or 1, $R_1$ and $R_2$ are each alkyl groups containing from 1 to 3 carbon atoms or are joined together to form a hetero-ring with the nitrogen atom and n is 1, 2 or 3. These compounds can be made by methods described in the prior art referred to above. Of the above-noted compounds, the diethylamino-derivative and the morpholino derivative are preferred.

The compounds usually are administered orally to achieve their effect. The oral administration generally is in tablet form with the active ingredient compounded with pharmaceutically-acceptable diluents. Any other convenient dosage form may be used.

The compounds exhibit a significant half-life after administration, thereby continuing to suppress acid formation for a significant period of time after administration.

Although clinical data in humans is required to determine useful dosage levels, it is possible to extrapolate expected human dosage levels from studies conducted in rats and reported in the Examples below. The following typical dosage levels are based on such rat studies. A typical dosage schedule for humans might consist of a 500 mg dosage of the active compound four times a day for one or two days as a loading dose, and then, as a result of the prolonged effect of the active, a single 250 to 500 mg dosage of active a day suffices.

The dosage of active compound which is administered to a patient after a loading dose of about 2 g generally is in the range of about 250 to about 500 mg. This dosage level is much less than the dosage level commonly presented for cimetidine, which is generally about 1.5 to about 2.5 g.

The compounds are effective in suppressing gastric acid formation and may be used alone or in combination with prostaglandins. It has been shown by experimentation that DPPE is effective in preventing stress-induced ulcer formation and alcohol-induced ulcer formation in rats. While clinical testing has not been performed, it is expected that the results obtained in rats will be repeated in humans.

EXAMPLES

EXAMPLE 1

This Example illustrates the effect of DPPE on restraint stress in rats.

Male Sprague-Dawley rats (200±10 g at the start of the experiments) in n=6 per group were randomly assigned to drug conditions and deprived of food but not water for 24 hours prior to the experiment. The rats were housed individually in a temperature, humidity and light-controlled environment.

The rats received a single intra-peritoneal injection of distilled water (vehicle) or DPPE in an amount of 8.0, 16.0 or 32.0 mg/kg immediately prior to being immobilized and placed into a cold environment for 3 hrs. Following this stress period, all rats were decapitated and blood from the cervical wound was collected in heparinized tubes, the plasma separated by centrifugation at 5000 kg per 15 minutes, and assayed for corticosterone.

The stomachs of the sacrificed rats were removed, opened along their greater curvature, rinsed with distilled water followed by 10% formaldehyde, and examined for ulcers under a dissecting microscope with an ocular micrometer. Both the number of ulcers per animal (ulcer frequency) and the cumulative ulcer length, expressed in millimeters (ulcer severity) were recorded.

The ulcer formation results obtained are summarized in the following Table 1:

TABLE 1

EFFECTS OF DPPE ON
RESTRAINT-STRESS ULCER FORMATION
(X ± S.E.M.)

| Treatment | Mean No. ulcers per rat | Mean Cumulative ulcer length (mm) |
|---|---|---|
| Vehicle | 18.0 (0.9) | 51.0 (4.1) |
| DPPE 8.0 mg/kg | 11.8 (1.1)** | 29.0 (2.4)** |
| DPPE 16.0 mg/kg | 9.8 (1.9)** | 17.5 (2.5)** |
| DPPE 32.0 mg/kg | 3.8 (1.0)* | 4.5 (0.7)* |

*Significantly less than all other groups ($p < .01$).
**Significantly less than vehicle group ($p < .01$).

It will be seen from this data that all doses of DPPE significantly decreased both the mean number of ulcers per rat and the mean cumulative ulcer length per rat. DPPE at the dosage of 32.0 mg/kg virtually eliminated the incidence and severity of restraint stress ulcers.

The plasma corticosterone data is summarized in the following Table 2:

TABLE 2

EFFECTS OF DPPE ON PLASMA
CORTICOSTERONE LEVEL
(X ± S.E.M.)

| Treatment | Mean Plasma Corticosterone level (ug %) |
|---|---|
| Non-stressed | 31.8 (2.8)* |
| Vehicle + stress | 68.3 (3.7) |
| DPPE 8.0 mg/kg + stress | 32.8 (2.3)* |
| DPPE 16.0 mg/kg + stress | 31.2 (3.5)* |
| DPPE 32.0 mg/kg + stress | 25.9 (1.9)* |

*Significantly less than vehicle + stress ($p < .01$).

As may be seen from the data in Table 2, all doses of DPPE significantly decreased the stress-induced rise in corticosterone to levels comparable to or below those seen in non-stressed animals.

EXAMPLE 2

This Example illustrates the effect of DPPE in suppressing gastric acid secretion in rats.

Rats of the type described in Example 1 were prepared with chronic, indwelling gastric cannulas. Following a 14-day post-operative recovery period, testing for the effects of DPPE on gastric acid secretion began. Rats (n=8) were given the following sequence of injections, each separated by 96 hours: distilled water, 8.0 mg/kg DPPE, 16.0 mg/kg DPPE, 32.0 mg/kg DPPE and distilled water.

For a given injection, the cannulas were opened and the stomach rinsed with 20 to 30 ml of warm distilled water to remove any residual food. Following a 30 min. draining period, collecting tubes and vials were connected to the cannulas and all secretions were collected for a 1 hr. pre-injection baseline period. At the beginning of the second hour, drugs or distilled water (vehicle) were administered, a second set of vials was attached to the collecting tubes and all secretions collected for another hour. At the beginning of the third hour, vials were again changed to obtain secretions for a final 1 hr. post-injection period.

Each animal, therefore, functioned as its own control and received vehicle, all doses of DPPE and vehicle again at 96 hr. intervals. The volume of secretion and total acid output (determined by titrating 1.0 ml aliquots to pH 7.0 with 0.01N NaOH), expressed as milli-equivalents of HCl per 100 g of body weight per hour, were recorded for each rat.

In a similar manner, following establishment of indwelling gastric cannulas and the recovery period, another group of rats (n=6), each serving as its own control, were injected with dimaprit (an $H_2$-agonist) to stimulate acid secretion in doses of 25, 50 and 100 mg/kg, each at 96 hr. intervals and the gastric secretions were collected as described above. The results of volume of secretion and total acid output then were compared to those of the same animals who, one hour prior to the injection of dimaprit at each concentration, received 32 mg/kg DPPE i.p.

The observed effects of DPPE on conscious basal gastric acid secretion are set forth in the following Table 3:

TABLE 3

EFFECTS OF DPPE ON BASAL (NON-STIMULATED)
GASTRIC ACID SECRETION (meq/100 g/h) (X ± S.E.M.)

| Treatment | Hour 1 (pre-injection baseline) | Hour 2 (injection) | Hour 3 (post-injection) |
|---|---|---|---|
| Vehicle 1 | 8.2 (1.8) | 12.1 (1.3) | 7.1 (1.1) |
| DPPE 8.0 mg/kg | 8.0 (2.2) | 3.4 (0.8)* | 4.7 (0.8)* |
| DPPE 16.0 mg/kg | 7.1 (1.8) | 3.6 (0.9)* | 1.9 (0.7)* |
| DPPE 32.0 mg/kg | 8.1 (1.7) | 1.1 (0.5)* | 0.5 (0.1)* |
| Vehicle 2 | 3.5 (1.1)* | 3.5 (0.9)* | 3.7 (1.2)* |

*Significantly less than vehicle 1 for hours 1, 2, or 3, respectively ($p < .05$)

It can be seen from Table 3 that all doses of DPPE significantly decreased gastric acid output immediately following ingestion and persisting into the third hour of gastric secretion collection. In all three hours of the collection period for the second vehicle ingestion, gastric secretion remained significantly below pre-DPPE levels, suggesting a long-term effect of high doses of DPPE on gastric acid secretion.

The effect of the $H_2$-agonist dimaprit ("Dim") is shown in Table 4:

TABLE 4

EFFECTS OF DIMAPRIT ± DPPE ON GASTRIC ACID SECRETION
(meq/100 g/h) (X ± S.E.M.)

| Treatment | Hour 1 (pre-injection baseline) | Hour 2 (injection) | Hour 3 (post-injection) |
|---|---|---|---|
| Vehicle 1 (saline) | 15.6 (3.3) | 14.1 (2.9) | 18.3 (2.9) |
| Dim 25 mg/kg | 20.3 (4.4) | 45.9 (5.3)* | 27.6 (3.8)* |
| DPPE 32 mg/kg + Dim 25 mg/kg | 18.6 (4.3) | 8.5 (1.1)** | 1.8 (0.6)** |
| Dim 50 mg/kg | 15.2 (3.5) | 59.4 (6.4)* | 76.5 (5.9)* |
| DPPE 32 mg/kg + Dim 50 mg/kg | 17.7 (2.9) | 4.9 (1.1).** | 9.5 (1.2)** |
| Dim 100 mg/kg | 15.8 (4.6) | 49.6 (4.7)* | 17.2 (4.3)* |
| DPPE 32 mg/kg + Dim 100 mg/kg | 18.5 (3.6) | 0.6 (0.1)** | 1.8 (0.4)** |
| Vehicle 2 (saline) | 17.9 (3.1) | 16.8 (3.3) | 22.1 (3.6) |

All values are X (± SEM).
*p < .05 vs. saline
**p < .05 DPPE + dim. vs. dim.

The optimal dose of the $H_2$-agonist appeared to be about 50 mg/kg, which resulted in a post-injection value for gastric acid of 76.5±5.9 meq/100 g/hr. When DPPE (32 mg/kg) was administered 1 hr. prior to the dimaprit, post injection values once again were significantly decreased below the maximally stimulated levels for all three dimaprit concentrations.

EXAMPLE 3

This Example illustrates the effect of DPPE administered orally to rats.

The procedure of Example 1 was repeated except that DPPE at a dosage level of 32.0 mg/kg and distilled water were administered orally instead of intraperitoneally (IP). The ulcer formation results, in terms of number of ulcers per animal (ulcer frequency), and the cumulative ulcer length (ulcer severity), are set forth in the following Table 5:

TABLE 5

Effects of Orally Administered DPPE on Stress Ulcer Formation (n = 6)

| Treatment | Mean (± SEM) No. Ulcers | Mean (± SEM) Ulcer Length |
|---|---|---|
| DPPE 32.0 mg/kg | 12.5 (1.8) | 7.9 (1.0) |
| vehicle | 18.0 (2.1) | 38.0 (5.9) |

As may be seen from Table 5, in comparison with the results set forth in Table 1 in Example 1, the oral administration is less effective than IP injection but significant protection was still obtained.

EXAMPLE 4

This Example illustrates the effects of DPPE in gastric ulcer formation induced by ethanol.

The procedure of Example 1 was repeated, except that the single intra-peritoneal injections were of saline followed one hour later by 100% ethanol and DPPE at a dosage level of 32.0 mg/kg followed one hour later by 100% ethanol. The ulcer formation results, in terms of number of ulcers per animal (ulcer frequency) and the cumulative ulcer length (ulcer severity), are set forth in the following Table 6:

TABLE 6

Effects of DPPE on Ethanol-Induced Gastric Ulcers (n = 6)

| Treatment | Mean (± SEM) No. Ulcers | Mean (± SEM) Ulcer Length (mm) |
|---|---|---|
| Saline + 100% ethanol | 9.8 (1.1) | 51.8 (2.3) |
| DPPE 32.0 mg/kg + 100% ethanol | 1.8 (0.2) | 2.3 (0.1) |

As may be seen from the results of the above Table 6, DPPE was able to virtually prevent ethanol-induced ulcer formation. These results suggest that DPPE is effective in preventing ulcers caused by irritant compounds, such as ethanol.

EXAMPLE 5

This Example illustrates the effect of a prostaglandin and DPPE on ulcer formation in rats.

The procedure of Example 1 was repeated, except that the IP administrations were of the prostaglandin "Cytotec" at a dosage level of 50 μg/kg, DPPE at a dosage level of 8.0 mg/kg and a mixture of 50 μg/kg of Cytotec and 80 mg/kg of DPPE. The ulcer formation results obtained are set forth in the following Table 7:

TABLE 7

Effects of DPPE and Prostaglandin $E_1$ (Cytotec) on Stress Ulcer Formation (n = 8)

| Treatment | Mean (± SEM) No. Ulcers | Mean (± SEM) Ulcer Length (mm) |
|---|---|---|
| Cytotec 50 μg/kg | 12.8 (3.1) | 9.8 (1.5) |
| DPPE 8.0 mg/kg | 13.3 (2.5) | 14.8 (1.3) |
| Cytotec 50 μg/kg + DPPE 8.0 mg/kg | 4.7 (2.7) | 5.9 (3.0) |

As may be seen from the results of Table 7, the addition of a suboptimal concentration of DPPE (i.e. 8 mg/kg) to a suboptimal concentration of prostaglandin (50 μg/kg) leads to additive or even synergistic effects.

EXAMPLE 6

This Example illustrates promotion of healing ulcers in rats using DPPE.

A first group of rats were subjected to restraint in the cold, as described in Example 1, and then were immediately treated with saline alone, 8 mg/kg of DPPE or 32 mg/kg of DPPE after the stress ulcers were induced. A second group of rats also were subjected to restraint stress and then received saline, 8 mg/kg of DPPE or 32 mg/kg of DPPE immediately after the ulcers were induced and then a second injection 24 hours later.

The ulcer healing effects obtained in comparison to control rats which were sacrificed immediately after stress, are set forth in the following Table 8.

TABLE 8

EFFECTS OF DPPE ON ULCER HEALING AT 24 AND 48 HOURS POST-STRESS

| Group | Drug | No. Ulcers | Ulcer Length (mm) |
|---|---|---|---|
| Control | — | 12.8 (2.2) | 34.0 (3.6) |
| 24 h post stress | saline | 4.8 (0.6) | 21.3 (2.9) |
| 24 h post stress | DPPE 8.0 | 3.8 (0.9) | 15.0 (2.2) |
| 24 h post stress | DPPE 32.0 | 2.8 (0.6) | 9.8 (1.3) |
| 48 h post stress | saline | 2.5 (0.2) | 7.8 (1.4) |
| 48 h post | DPPE 8.0 | 1.8 (0.4) | 4.8 (0.6) |

TABLE 8-continued
EFFECTS OF DPPE ON ULCER HEALING AT 24 AND 48 HOURS POST-STRESS

| Group | Drug | No. Ulcers | Ulcer Length (mm) |
|---|---|---|---|
| stress 48 h post stress | DPPE 32.0 | 0.0 (0.0) | 0.0 (0.0) |

As may be seen from the results set forth in this Table 8, at 24 hours, while the saline-injected rats still had about 21 mm of ulceration, the animals which received the single injection of 8 mg/kg of DPPE had only 15 mm and of 32 mg/kg of DPPE had under 10 mm of ulceration.

In addition, for the rats having two injections, whereas the saline group still had 8 mm of ulceration at 48 hours, the 8 mg DPPE and the 32 mg DPPE groups had no ulcers at all.

These data indicated that DPPE promotes healing of ulcers after their formation as well as inhibiting ulcer formation under ulcer-inducing conditions.

SUMMARY OF DISCLOSURE

In summary of this disclosure, the present invention provides a novel and effective method of treating and inhibiting gastro-intestinal ulcer disorders, by administering certain compounds, including DPPE and its homologs. Modifications are possible within the scope of this invention.

What we claim is:

1. A method of promoting the healing of stress- and irritant-induced ulcers, which comprises administering to the gastrointestinal tract an effective amount of at least one diphenylmethane compound having the formula I:

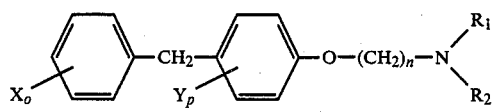

wherein X and Y are each chlorine or bromine, o and p are 0 or 1, $R_1$ and $R_2$ are each alkyl groups containing from 1 to 3 carbon atoms or are joined together to form a morpholino group with the nitrogen atom and n is 1, 2 or 3.

2. The method of claim 1 wherein

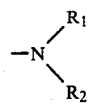

is a diethylamino group.

3. The method of claim 1 wherein n is 2.
4. The method of claim 1 wherein o and p are each 0.
5. The method of claim 1 wherein n is 2, o and p are each 0 and

is a diethylamino group.

6. The method of claim 1 wherein said compound is administered orally.
7. The method of claim 6 wherein said compound is administered orally in the form of an admixture of an effective amount thereof with a pharmaceutically-acceptable carrier therefor.
8. The method of claim 3 wherein said compound is administered in the form of a tablet.
9. The method of claim 1 wherein said compound is administered orally in an amount of from about 250 to about 500 mg per day after a loading dosage of about 500 mg/dosage four times a day for 1 to 2 days has been administered.
10. A pharmaceutical composition useful for inhibiting or healing an ulcerous condition of the gastrointestinal tract, which comprises an effective amount of at least one diphenylmethane compound of the formula:

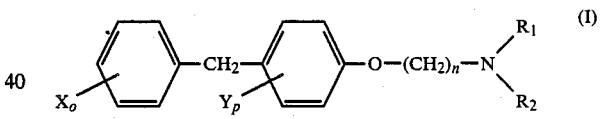

wherein X and Y are each chlorine or bromine, o and p are 0 or 1, $R_1$ and $R_2$ are each alkyl groups containing from 1 to 3 carbon atoms or are joined together to form a morpholino group with the nitrogen atom and n is 1, 2 or 3, at least one prostaglandin and a pharmaceutically-acceptable carrier.

* * * * *